US012564730B2

(12) United States Patent
Assa et al.

(10) Patent No.: US 12,564,730 B2
(45) Date of Patent: Mar. 3, 2026

(54) LASER SURGICAL APPARATUS FOR PERFORMING TREATMENT BY IRRADIATING A PART TO BE TREATED BY A VARIABLE PULSED LASER BEAM

(71) Applicant: Acclaro Corporation, Smithfield, RI (US)

(72) Inventors: Shlomo Assa, Smithfield, RI (US); Yingyuan Fang, Smithfield, RI (US)

(73) Assignee: ACCLARO CORPORATION, Smithfield, RI (US)

( * ) Notice: Subject to any disclaimer, the term of this patent is extended or adjusted under 35 U.S.C. 154(b) by 0 days.

(21) Appl. No.: 17/073,524

(22) Filed: Oct. 19, 2020

(65) Prior Publication Data

US 2022/0118277 A1 Apr. 21, 2022

(51) Int. Cl.
*A61N 5/06* (2006.01)
*A61N 5/067* (2006.01)

(52) U.S. Cl.
CPC .... *A61N 5/0616* (2013.01); *A61N 2005/0627* (2013.01); *A61N 5/067* (2021.08)

(58) Field of Classification Search
CPC .................. A61N 5/0616; A61N 5/067; A61N 2005/0627
See application file for complete search history.

(56) References Cited

U.S. PATENT DOCUMENTS

| | | |
|---|---|---|
| 5,257,706 A | 11/1993 | McIntyre |
| 5,458,596 A | 10/1995 | Lax |
| 5,689,520 A | 11/1997 | Hoang |
| 6,193,711 B1 | 2/2001 | Connors |
| 6,277,116 B1 | 8/2001 | Utely |
| (Continued) | | |

FOREIGN PATENT DOCUMENTS

| | | |
|---|---|---|
| JP | 2009533197 A | 9/2009 |
| JP | 2019535427 A | 12/2019 |
| (Continued) | | |

OTHER PUBLICATIONS

Nanni et al., "Complications of carbon dioxide laser resurfacing, An evaluation of 500 paitents" American Society for Dermatol Surg, 24, pp. 315-320, 1998.

(Continued)

*Primary Examiner* — Lynsey C Eiseman
*Assistant Examiner* — Jessica L Mullins
(74) *Attorney, Agent, or Firm* — Panitch Schwarze Belisario & Nadel LLP

(57) ABSTRACT

A laser surgical apparatus for performing treatment by irradiating a part to be treated by a variable pulsed laser beam is disclosed. This apparatus includes a laser source which emits variable waveform output of treatment laser beam pulses; a flexible beam delivery for delivering the treatment laser beam emitted from the laser source, the flexible beam delivery includes at the distal end automated optical scanner comprising of 2 moving mirrors; and a surgical instrument is connected to an end of the scanner and used for irradiating the treatment laser beam delivered therein to the treatment part. By having the ability to vary the laser's output pulse frequency, pulse width, and pulse energy, multiple tissue effects can be achieved using one laser surgical apparatus.

12 Claims, 6 Drawing Sheets

(56) References Cited

U.S. PATENT DOCUMENTS

| | | | |
|---|---|---|---|
| 7,951,139 B2 | 5/2011 | Assa | |
| 7,957,440 B2 | 6/2011 | Boutoussov | |
| 8,202,268 B1 | 6/2012 | Wells | |
| 9,005,262 B2 | 4/2015 | Liu | |
| 9,414,888 B2 | 8/2016 | Liu | |
| 2001/0016732 A1 | 8/2001 | Hobart et al. | |
| 2004/0133190 A1 | 7/2004 | Hobart et al. | |
| 2006/0129141 A1 | 6/2006 | Lin | |
| 2008/0234669 A1 | 9/2008 | Kauvar | |
| 2009/0131922 A1* | 5/2009 | Dewey | A61B 18/203 606/9 |
| 2012/0232537 A1 | 9/2012 | Liu et al. | |
| 2013/0096546 A1* | 4/2013 | Mirkov | A61B 18/22 606/9 |
| 2014/0018783 A1* | 1/2014 | Modi | A61N 1/0472 606/9 |
| 2014/0364870 A1 | 12/2014 | Alvarez et al. | |
| 2015/0202007 A1* | 7/2015 | Manstein | A61B 18/203 606/9 |
| 2017/0112574 A1* | 4/2017 | Cohen | A61B 18/22 |
| 2018/0140866 A1 | 5/2018 | Daly et al. | |
| 2018/0296269 A1 | 10/2018 | Bhawalkar et al. | |
| 2021/0135424 A1* | 5/2021 | Bacher | H01S 3/1306 |

FOREIGN PATENT DOCUMENTS

| | | | |
|---|---|---|---|
| KR | 20150044772 A | 4/2015 | |
| WO | 2010145802 A1 | 12/2010 | |
| WO | 2011084863 A2 | 7/2011 | |

OTHER PUBLICATIONS

Int'l Search Report and Written Opinion issued Mar. 18, 2022 in Int'l Application No. PCT/US21/63497.

Int'l Search Report and Written Opinion issued Feb. 23, 2022 in Int'l Application No. PCT/US21/62159.

Office Action issued Apr. 2, 2024 in U.S. Appl. No. 17/113,588.

Lukac et al., "Dual Tissue Regeneration: Non-Ablative Resurfacing of Soft Tissues with FotonaSmooth Mode Er:YAG Laser", 2018, Journal of Laser and Health Academy (2018).

Extended European Search Report issued Jul. 23, 2024 in European Application No. 21904228.0.

Partial European Search Report issued Jun. 18, 2024 in European Application No. 21884077.5.

* cited by examiner

LASER SURGICAL APPARATUS FOR PERFORMING TREATMENT BY IRRADIATING A PART TO BE TREATED BY A VARIABLE PULSED LASER BEAM

TECHNICAL FIELD

The present disclosure is related to radiation-based dermatological treatment devices and methods, e.g., laser-based devices for providing fractional treatment, or devices using any other type of radiation source for providing any other suitable type of dermatological treatment. Some embodiments include an automated scanning system for scanning a beam to multiple locations on the skin in particular to treat cosmetic conditions affecting the skin of various body parts, including face, neck, and other areas traditionally prone to wrinkling, lines, sagging and other distortions of the skin.

BACKGROUND

This specification relates to a laser surgical apparatus having the ability to emit plurality of treatment pulses using the optical scanner and different types of surgical instruments to be used in surgery on soft human living tissue.

Exposure of the skin to environmental forces can, over time, cause the skin to sag, wrinkle, form lines, or develop other undesirable distortions. Even normal contraction of facial and neck muscles, e.g. by frowning or squinting, can also over time form furrows or bands in the face and neck region. These and other effects of the normal aging process can present an aesthetically unpleasing cosmetic appearance.

Accordingly, there is well known demand for cosmetic procedures to reduce the visible effects of such skin distortions. There remains a large demand for "tightening" skin to remove sags and wrinkles especially in the regions of the face and neck.

There have been known laser surgical apparatus for performing treatment by irradiating a part to be treated by a laser beam. For instance, a laser treatment apparatus which emits a carbon dioxide laser beam having infrared wavelengths has been used in plastic surgery treatments for removing wrinkles, birthmarks, etc. of patients.

Light-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering light or laser radiation to an area of tissue on a person's body, e.g., the skin or internal tissue, to treat the tissue in a photochemical, photobiological, thermal, or other manner, which can be ablative or non-ablative, among other properties, depending on the particular application.

Light-based treatment devices include various types of radiation sources, such as lasers, LEDs, flashlamps, etc. For example, laser diodes are particularly suitable for certain light-based treatments and devices for providing such treatments. Laser diodes are compact, as they are typically built on one chip that contains the major necessary components for light generation other than a power source. Further, laser diodes typically provide an efficiency of up to 50% or higher, which enables them to be driven by low electrical power compared to certain other lasers. Laser diodes allow direct excitation with small electric currents, such that conventional transistor based circuits can be used to power the laser.

Other characteristics typical of laser diodes include high temperature sensitivity/tunability, and a highly divergent beam compared to certain other lasers. Laser diodes typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-based treatment devices typically include optics downstream of the laser source to scan, shape, condition, direct, and/or otherwise influence the laser radiation to the target tissue as desired. Such optics may include lenses, mirrors, and other reflective and/or transmissive elements, for controlling optical parameters of the beam, such as the direction, propagation properties or shape (e.g., convergent, divergent, collimated), spot size, angular distribution, temporal and spatial coherence, and/or intensity profile of the beam, for example. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide complete coverage of a target area of tissue. For other applications, e.g., certain wrinkle treatments, vascular treatments, pigmentation treatments, anti-inflammatory treatments, and other skin rejuvenation treatments, the scanned radiated areas may be spaced apart from each other by non-irradiated areas such that only a fraction of the overall target area of the tissue is radiated during a treatment session. Thus, in such applications, there are generally regions of untreated tissue between regions of treated tissue. This type of treatment is known as "fractional" treatment (or more specifically, fractional photothermolysis in some cases) because only a fraction of the target area is irradiated during a treatment session.

Some known scanning systems move the radiation source itself relative to the device housing or structure in order to form the scanned pattern of radiated areas. Other known scanning systems utilize one or more moving optical elements (e.g., mirrors and/or lenses) in order to scan a radiation beam into a pattern of radiated areas, rather than moving the radiation source relative to the device housing or structure.

Liu et al. U.S. Pat. No. 9,414,888 B2 is a hand-held device for providing laser-based dermatological treatments includes a laser beam source supported in a device body, an automated scanning system, and control electronics. The automated scanning system is configured to receive an input beam generated by the laser beam source and scan the input beam to provide a series of output beams for delivery to the skin via an application end of the device to form a pattern of treatment spots on the skin.

Chan et al. US 2011/0098.691 A1 teaches a fractional treatment system, an adjustable mechanism can be used to adjust the beam shape, beam numerical aperture, beam focus depth, and/or beam size to affect the treatment depth and or the character of the resulting lesions. Adjustment of these parameters can improve the efficiency and efficacy of treatment.

Another method surgically resurfaces facial skin by ablating the outer layer of the skin (from 200 μm to 600 μm), using laser or chemicals. In time, a new skin surface develops. The laser and chemicals used to resurface the skin also irritate or heat the collagen tissue present in the dermis. When irritated or heated in prescribed ways, the collagen tissue partially dissociates and, in doing so, shrinks. The shrinkage of collagen also leads to a desirable "tightened" look. Still, laser or chemical resurfacing leads to prolonged redness of the skin, infection risk, increased or decreased pigmentation, and scarring.

Connors et Al. in U.S. Pat. No. 6,193,711 B1 Rapid Pulse Er:YAG Laser teaches about a new Er:YAG laser system that has a resonant cavity including an Er:YAG rod pulse-pumped by a pulsed flashlamp for the purpose using on human tissue as It has been known for some time that tissue ablation can be enhanced through the use of infrared wavelengths that more closely match absorption peaks of water, the major constituent in biological tissue.

Many of the Laser radiation use on the skin will create an unwanted side effect known as PIH-Post Inflammatory Hyperpigmentation. This is the skin reaction to access thermal damage due to laser radiation treatment. 70% of darker skin will response with sever PIH to conventional laser treatment which makes it so much more challenging especially for patients with darker skin such as Asian or Latin patients.

Alternative treatments that are not laser based are explored to get the results expected and reduce or eliminate the risk associated with the patient's skin developing PIH. PIH complications is a significant barrier for laser system to treat human skin for the purpose of skin rejuvenation. It is highly desired to bring a laser system that can treat all skin types without the risk of PIH.

One of these different approaches described in Lax et al. U.S. Pat. No. 5,458,596 details the use of radio frequency energy to shrink collagen tissue. This cosmetically beneficial effect can be achieved in facial and neck areas of the body in a minimally intrusive manner, without requiring the surgical removal of the outer layers of skin and the attendant problems just listed. The use of RF system such as the said system is to aimed to treat darker skin types without causing PIH.

Utely et al. U.S. Pat. No. 6,277,116 also teaches a system for shrinking collagen for cosmetically beneficial purposes by using an electrode array configuration.

However, areas of improvement remain with the previously known systems. In one example, fabrication of an electrode array may cause undesired cross-current paths forming between adjacent electrodes resulting in an increase in the amount of energy applied to tissue.

In another example, when applying the array to tissue, the medical practitioner experiences a "bed-of-nails". In other words, the number of electrodes and their configuration in the array effectively increases the total surface area of the electrode array. The increase in effective surface area then requires the medical practitioner to apply a greater force to the electrode array in order to penetrate tissue. Such a drawback may create collateral damage as one or more electrode may be placed too far within the skin. Additionally, the patient may experience the excessive force as the medical practitioner increases the applied force to insert the array within tissue.

Thermage, Inc. of Hayward Calif. also holds patents and sells devices for systems for capacitive coupling of electrodes to deliver a controlled amount of radiofrequency energy. This controlled delivery of RF energy creates an electric field that generates "resistive heating" in the skin to produce cosmetic effects while cooling the epidermis to prevent external burning of the epidermis.

In such systems that treat in a non-invasive manner, generation of energy to produce a result at the dermis results in unwanted energy passing to the epidermis. Accordingly, excessive energy production creates the risk of unwanted collateral damage to the skin.

Another device that is very popular among Asian people is micro-needle roller. This device is used by the patient to roll the needles over their facial skin creating many tiny open injuries in the epidermis, thereafter enabling the method of delivering a drug through the skin (percutaneous), since the drug hardly passes through the stratum corneum, the absorption rate of the drug is very low. In particular, the higher the molecular weight of the drug, the lower the drug absorption rate. In order to improve the above problem, a technique using a microneedle has been proposed. According to the technique, a channel passing through a part or the whole of the epidermis layer is formed by microneedles, and then a drug is transmitted through the channel to the epidermis layer or its lower layer.

JP2009533197A—"Micro needle roller assembly" provides a microneedle roller assembly according to the present invention includes a cylindrical outer member having a plurality of microneedles mounted on a surface thereof, and an inner member positioned inside the outer member and supported by the outer member by a support piece. A roller head and a handle portion coupled to the internal member and rotating the internal member of the roller head, wherein the microneedle, the cylindrical external member, and the internal member are made of a polymer resin.

In view of the above, there remains a need for an improved energy delivery system. Such systems may be applied to create improved electrode array delivery system for cosmetic treatment of tissue. In particular, such an electrode array may provide deep uniform heating by applying energy to tissue below the epidermis to causes deep structures in the skin to immediately tighten. Over time, new and remodeled collagen may further produce a tightening of the skin, resulting in a desirable visual appearance at the skin's surface.

SUMMARY OF THE INVENTION

The present disclosure is related to radiation-based dermatological treatment devices and methods, e.g., laser-based devices for providing fractional treatment.

Therefore, in view of the foregoing, it is an object of the present invention to provide a solution for safe laser surgical treatment for all skin colors that reduces the risk of PIH. Asian and Latin born skin type 3 and 4 most commonly will respond to conventional treatment by developing PIH. Recent study by C. A. Nanni & T S Alster, "Complications of carbon dioxide laser resurfacing. An evaluation of 500 patients" analyzed large population of patients with complication after being treated with Golden Standard CO2 fractionated laser device. This study revealed that 37% of white skin patients (skin type 1-2) will develop PIH after laser treatment. The same report outlines that 70% of darker skin commonly Asian and Latin patients will develop PIH after treatment with fractionated CO2 laser. This statistic is acceptable in the market. The risk of PIH after a conventional fractionated laser treatment is known as the industry barrier to entry. In Asia countries like China or Korea conventional fractionated laser devices will not be suitable to use on darker Asian skin types 3-4 due to the high probability of the patient developing PIH.

Developing PIH as a reaction to conventional fractionated laser treatment is an industry barrier that prevent both treating Physician and patient from using these devices to rejuvenate darker skin. But at the same time, Asian population continues to grow, and today Asian are making about 60% of the world population. Asian countries like China, Korea and others having large increase of population, and also significant economic growth that creates a very wealthy middle class having the financial means to seek anti-aging aesthetic treatment. This trend is continuing in spite of the risks associated with conventional treatment, and it emphasizes the unmet need that exist today in Asian countries.

Also, in Asian culture-Physical appearance is extremely important for social acceptance and employment opportunities. People line up in clinics for aesthetic treatment before job interviews. The importance of physical appearance is also increased because of frequent use of social media among Asians, who want to look in their best in every selfie and every post.

The situation is similar in both Latin Middle East countries with large percentage of the population with darker skin types 3-4.

In Asia region, alternative solutions to combat aging providing solutions like Micro needles rollers that will perforate the epidermis with many tiny holes enabling a quick and effective way to deliver skin anti-aging drugs that usually are not effective through the skin. Since the use of micro-needle roller creates a potential health hazard and high probability for contamination, it is yest another objective of this invention to provide a device that can create mechanical tiny holes in the skin that will eliminate the infection and other risks and will provide the effective way to deliver the anti-aging drugs through the tiny holes in the skin.

It is yet further objective of this invention to provide a device and a method to treat all skin types, especially Asian skin type 3-4 with fractionated laser device to combat signs of aging but with minimizing the risks for PIH, opening the possibilities to these individuals with darker skin type to recognize the opportunity and to get fractionated rejuvenation treatments. It is further yet another objective of this invention to apply laser energy to human skin is a manner that will create an tinny openings in the epidermis by using that said laser beam to enable to apply drugs to penetrate the skin without the need to apply the micro-needles to puncture the skin. It is the objective of this invention to create the skin perforation but with no contact eliminating further complications from contaminations and with minimal thermal injuries that can cause PIH reaction.

It is further yet another objective of this invention, to enable the treatment of skin by ablating a tinny opening in the epidermis and into the dermis and using the said laser beam in different operating modalities to create a control thermal injury in addition to the mechanical injury in such a way that the natural healing process will create younger and better looking human skin to reverse the signs of aging, and at the same time because of the great level of control of the thermal injury to avoid any form of complications to human skin after the said laser treatment including but not limited to PIH. The particular objective of this invention is to create a blended pulse regime that will create an effective ablation of human skin with cold injury and to add a controlled thermal injury that will enhance the healing results but without adding risks from excessive thermal injury like PIH.

It is yet another further objective of this invention to provide an optimized solution for fractionated laser based skin rejuvenation device that will be safe and effective on all skin types minimizing the risk of side effects especially minimizing the risk of PIH.

It is yet another further objective of this invention to provide a safe and effective device for laser surgical scalpel that can be used in general surgery provide significant advantages to the patient healing prospect using the said laser in the same manner to efficiently cold cut tissue and blend pulses that will add controlled thermal injury that is necessary to coagulate the said cut tissue to stop any bleeding at the said cut.

It is yet another objective of this invention to use a very small diameter tool to ablate and coagulate human tissue in areas that are very hard to reach like inside ethe human eye or treating human vocal cord tissue. In this yet another objective, the laser will be delivered to the treated tissue by using a very small fiber optic device that will enable the physician to reach small cavities, and at the same time use the said laser with blended pulses that can ablate the necessary tissue and create a controlled coagulation to eliminate un necessary bleeding, but without any risk to cause unwanted and excessive thermal injuries that may lead to side effect especially when treating such delicate and important human tissues such as human eye tissue or human vocal cord.

It is therefore an object of this invention to provide a device and method to treat human tissue in a way that will create the positive results such as reversing aging signs and at the same time will overcome the drawbacks of the prior art by minimizing unwanted thermal injury.

BRIEF DESCRIPTION OF THE DRAWINGS

The invention will now be described with reference to the accompanying drawing which is a plain illustrative view of the apparatus which operates in accordance with the method for the invention.

DETAILED DESCRIPTION OF THE INVENTION

Figure 1A:
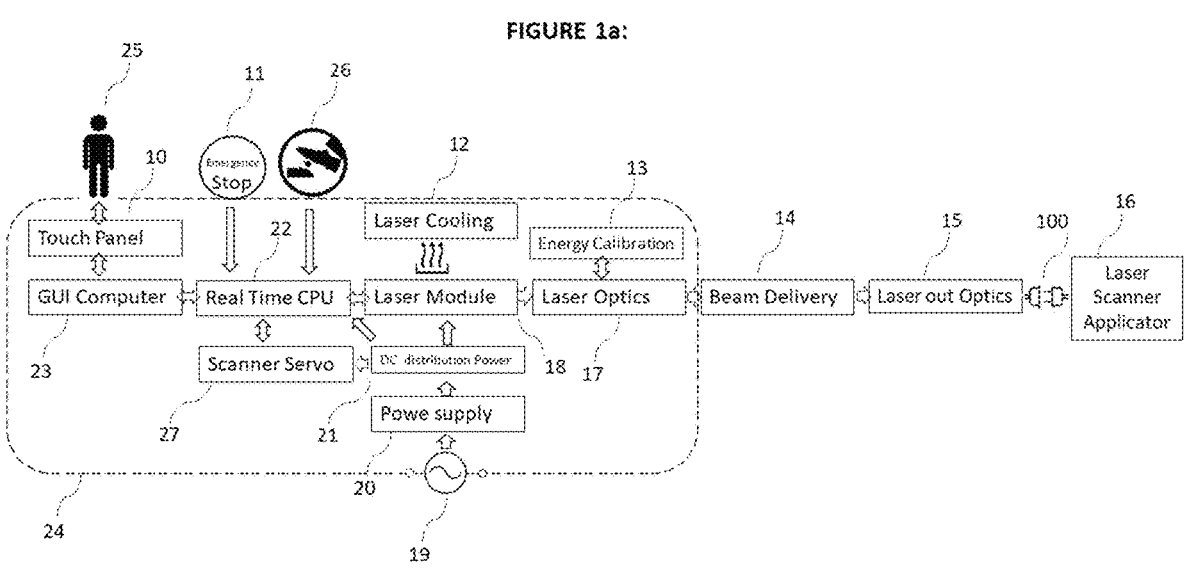
FIG. 1a schematically illustrates one preferred embodiment of a laser system in accordance with the present invention.

Some embodiments of the disclosure may be understood by referring, in part, to the following description and the accompanying drawings, in which like reference numbers refer to the same or like parts.

FIG. 1 illustrates various components of one preferred embodiment of radiation-based treatment device 24. Radiation-based treatment device 24 may include a radiation source 18 including a radiation source 18 configured to generate an energy beam. In another preferred embodiment the Radiation-Based device will be a laser device, and in another embodiment the Radiation-Based device may be a fiber laser device. The said Radiation-Based device is powered with direct current (DC) that is generated by medical power supply 20. The power supply 20 is configured to accept wide range of alternate current supply commonly used in different countries like USA 110V and 60 HZ or Germany using 240V and 50 HZ. The said power supply 20 will convert the alternate current to a direct current, and in one preferred embodiment that working DC voltage produced by power supply 20 will be 24 volts. The electric energy necessary to control the entire radiation-based device 24 will be conditioned by DC distribution power device made in printed circuit device 21. The DC distribution power printed circuit device 21 supply electric power to all the components in the said preferred embodiment device. The Radiation-Based device 18 is powered by electric energy provided by the DC distribution power 21, while the laser energy command signal is provided by the Real Time CPU 22. In this preferred embodiment the Real Time CPU 22 commands will be control by another computer, GUI Computer 23. In this preferred embodiment, the GUI Computer 23 has a touch panel that used by the device operator 25 to enter the desired command such as radiation-based device energy settings. Once the operator 25 enters the desired radiation-based desired device setting the GUI Computer 23 will communicate the desired program to the Real Time CPU 22 to feed the Radiation-Based device the desired energy setting by the Operator 25. The Radiation Based device will generate the desired laser energy. During operations, the radiation-based device 18 will generate access heat that will be dissipated to the surrounding to cool the device. In one of the preferred embodiments the radiation based Device 18 is a mid IR fiber laser that in yet another preferred embodiment operates at 2,940 nm. In yet another preferred embodiment the radiation device 18 may be an ER; YAG laser operation at 2,940 nm, and in yet another preferred embodiment the radiation device 18 may be ER:YSGG laser operating at 2,780 nm. In the said preferred embodiment laser cooling device 12 will extract the access heat from the radiation device, said mid IR fiber laser and dissipate it to the surrounding using cooling fan. In the said preferred embodiment, the mid IR fiber laser emission will radiate into the laser optic module 17. In the preferred embodiment, the laser optics module 17 will collimate the laser beam to about 7 mm in diameter and combine a visible red laser operating around 650 nm to enable the operator 25 to see the location and pointing of the mid IR beam as it is invisible. In yet another preferred embodiment the laser optics module 17 will be connected to energy calibration device 13. In the preferred embodiment the energy calibration device is a InAsSb Photovoltaic Detector that is optimized to measure laser radiation at the preferred embodiment said range of 2,940 nm. The said detector is design to read a sample of the main laser beam in real time to control the energy per pulse is such a manner that when the energy set by the Operator 25 had been delivered and measured by the Energy Calibration detector 13 a command will be sent to the real time CPU Controller 22 to cut the laser pulse energy as the delivered set energy is achieved. In the said preferred embodiment the Energy Calibration detector 13 is a real time servo controller to ensure that the said energy delivered is identical to the energy set by Operator 25. The said detector is measuring a sample of the laser energy and monitoring in close loop the energy setting selected by the Operator 25. In one preferred embodiment the Radiation based device 24 includes a Scanner Servo controller 27 that is used to drive X and Y scanner motors, The Scanner Servo controller is powered by DC distribution power 21, that is regulating the DC voltage converted from AC voltage by Power supply 20. The command to move X and Y scanner motors is selected by Operator 25, entering the commands using Touch panel 10 that is connected to GUI Computer 23. The Operator 25 command is transferred to Real time CPU controller 22 that sends commanding signals to Scanner servo controller 23 to move the scanners in Applicator 16.

The radiation energy will be directed to a beam delivery device 14. In one preferred embodiment the beam delivery 14 will be a fiber optics device able to transmit the emission. In yet another preferred embodiment the beam delivery may be 7 rotating mirrors articulated arm. The laser energy will be directed to the final energy conditioning device, laser output optics 15. In one of the preferred embodiment the laser out optics 15 may be another collimating optics to collimate the laser beam to ø7.0 mm, and in yet another preferred embodiment the laser out optics 15 may be a protective and replaceable window to prevent dust and contaminations from effecting the radiation based device 18 from operating reliability.

In yet another preferred embodiment the laser out optics 15 includes a quick disconnect connection 100 that may allow the Operator to replace the laser applicator 16 in use to achieve different clinical effects as will be disclosed later. To operate the radiation based laser energy the Operator 25 will use a footswitch device 26 to command the energy emission to be delivered as the setting that the Operator 25 determined and entered to the GUI Compute 23 using the Touch Panel 10 herein. When the Operator 25 wants to stop the Radiation Based device emission, he will de-press the footswitch 26 to stop the laser operations. In case of emergency the Operator 25 may stop the Device 24 from operating by pressing the emergency switch 11.

Figure 1B:
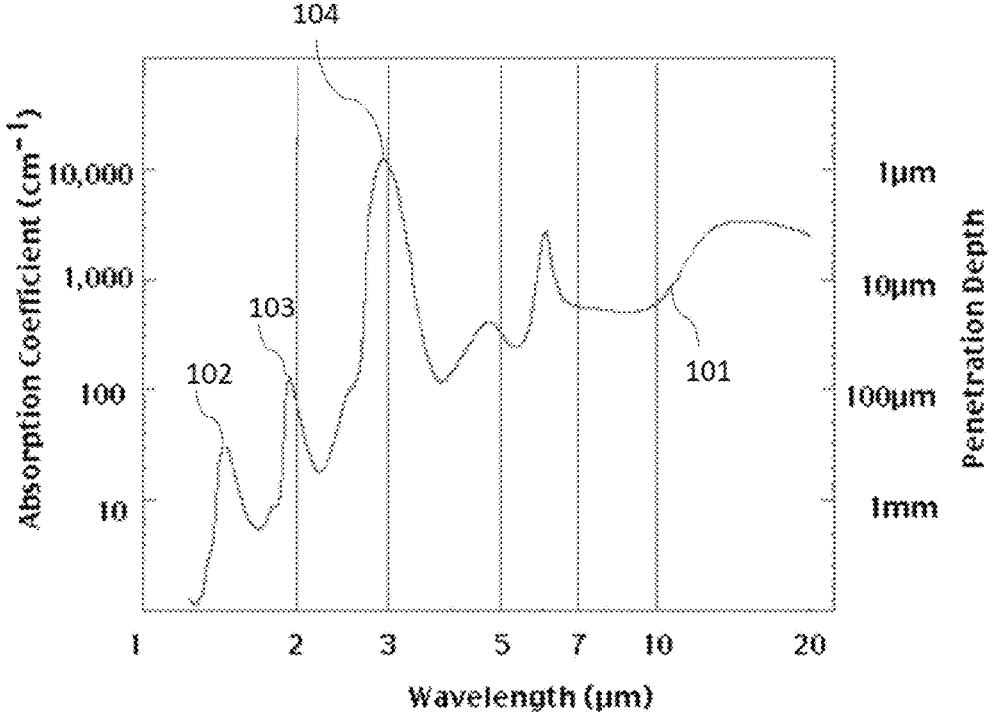
FIG. 1b is a schematic illustration of a absorption coefficient of water in infra-red range of optical wavelengths.

FIG. 1*b* illustrates the absorption coefficient of water in the infra-red radiation wavelengths. It is important to note that human tissue contains about 70% water, making water absorption a very effective tool to treat human tissue. The basic mechanism of action of radiation based devices is selective photo thermolysis, which is matching the radiation device wavelength to a light absorbing chromophore to create the selected effects. In one of the preferred embodiments the selected wavelength may be 2,940 nm. As FIG. 1*b* illustrates, 104 is the point of peak water absorption of 11,700 cm$^{-1}$, at wavelength of 2,940 nm, the highest water absorption in the infra-red spectrum. To compare water absorption to other commonly used radiation-based device for treating human tissue, 101 is absorption coefficient of 850 cm$^{-1}$ for 10,600 nm of carbon dioxide ($CO_2$) laser devices. Comparing the water absorption value by a carbon dioxide ($CO_2$) laser to the one preferred embodiment mid IR fiber laser operating at 2,940 nm, concluding that the ablation effectiveness of water by the said mid IR fiber laser operating at 2,940 nm is 13.7 time better, equal to the absorption coefficient ratio of said fiber laser to carbon dioxide lasers of $$13.7 = \frac{11,700}{850}.$$

The said preferred embodiment device operating at 2,940 nm will ablate the water in human tissue 13.7 time more efficient, requiring 13.7 times less optical energy and therefore may be producing 13.7 times less potential thermal injury to the treated tissue. FIG. 1b illustrated, 103 is water absorption for 1,927 nm which another fiber laser commonly used in treating human tissue with absorption coefficient of 114 cm$^{-1}$, about 100 time less than one of the preferred embodiment operating at 2,940 nm. As can be seen this radiation-based device is still been characterized as ablative device capable of adapting human tissue by targeting water, however, with very low ablation efficiency and with large potential unwanted thermal injuries. As another comparison, FIG. 1b illustrates, 102 is water absorption at 1,550 nm, value of 10 cm$^{-1}$, This radiation based device operating at 1,550 nm is classified already as a non-ablative device, as the water absorption coefficient is too low compared with the peak water absorption characteristics of one of the preferred embodiment.

Figure 2:
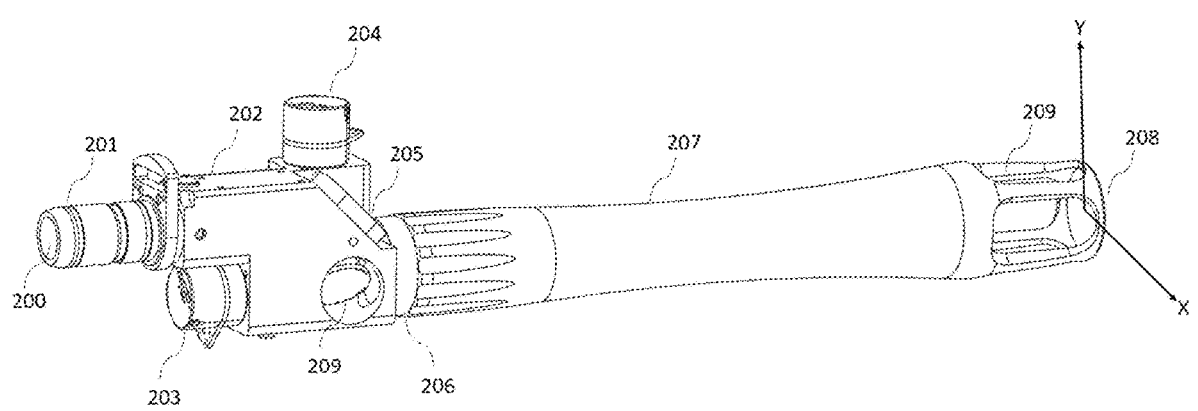
FIG. 2 is a schematic illustration of one preferred embodiment of a laser scanner applicator attachment in accordance with the present invention.
Figure 3A:
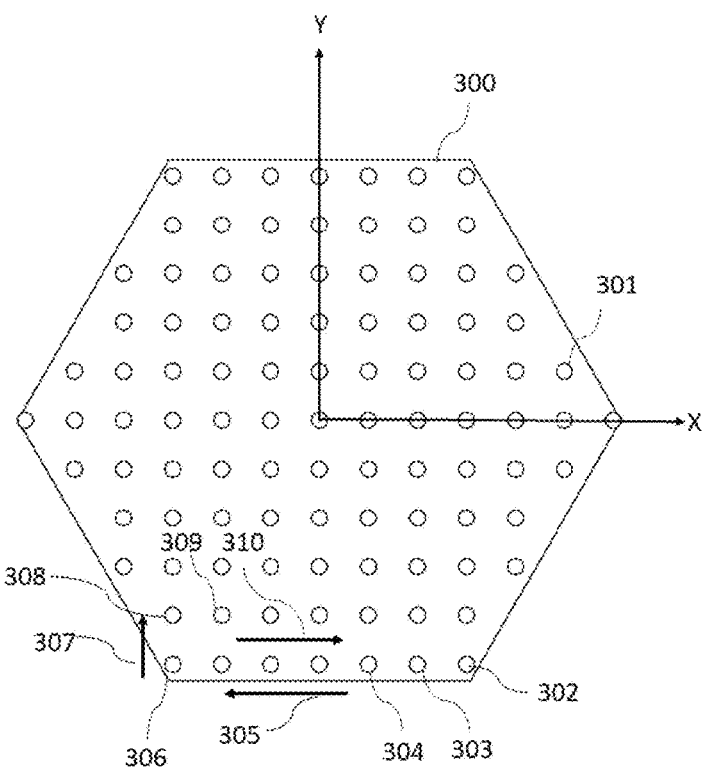
FIG. 3a-d are a schematic illustration of one preferred embodiment of a fractionated laser treatment pattern place on the desired treated tissue, in accordance with the present invention.

FIG. 2 illustrates one preferred embodiment of Scanner Applicator to be used to treat human skin for facial rejuvenation. This Application may be connected to the radiation-based treatment device 24 illustrated in FIG. 1a. connecting the Applicator 16 using the quick disconnect 100. FIG. 2 illustrates the location of the human skin to be treated, 208. The field of treatment is defined by X and Y axis to denote the scanning action directions. The Applicator tip is part of the Applicator handpiece 207 that enables the Operator to clearly see the field of treatments via opening 209 in the handpiece tip. In the said preferred embodiment this handpiece is made of metal design for multiple use and it is removable using threaded mount to housing 206. In yet another preferred embodiment the handpiece is one-time disposable use made of a medical grade plastic that will be recycled after every treatment. The handpiece 207 is mounted on to lens housing 206, which include the laser focusing lens. In one preferred embodiment the focusing lens in use has focal distance of 150 mm, and the laser focus spot size will be 120 µm. The lens housing 206 has a mounting thread on one end fitted to mount the handpiece 207 threads, and at the other end the lens housing 206 is permanently mounted to the scanner housing 202. In this one preferred embodiment, the scanner housing 202 is permanently connected to the mounting shaft 201 which is the quick disconnect used to connect the applicator to the Radiation Based device 24 of FIG. 1a using quick disconnect 100. Mounting shaft 201 is hollow and enables the laser beam to propagate to the scanner applicator via aperture 200. In the said preferred embodiment the incoming laser beam entering the scanner applicator via aperture 200 is collimated to ø7 mm and propagating at the same direction as the output focus beam is propagating toward the treatment human skin target at 208. In the said preferred embodiment the input laser beam entering at aperture 200 will be reflected 90° vertically, in Y Axis direction shown in FIG. 2, by a permanently mounted reflecting mirror 205. The laser beam than will be reflected again in the horizontal-X direction by a mirror 209 which is mounted on Y axis Scanner Motor 203 that is permanently mounted into the Scanner housing 202. The said mirror 209 can be rotated is small angles by powering the scanner motor allowing the reflected beam to move in the Y direction any time that the mirror 209 will be moved by electronic signal. The laser beam propagating from mirror 209 that is connected to scanner motor 203 in the −X direction will be reflected the same way by a mirror that is mounted on the X axis motor 204, and therefore can be moved in X direction every time that electronic command will turn the mirror of scanner motor 204. In the said preferred embodiment, scanner motor 203 will drive the mirror reflecting the laser beam creating laser beam motion in the ±Y direction of 208, and the scanner motor 204 will drive the mirror reflecting the laser beam creating laser beam motion in the ±X direction. The electronic signal can drive both Scanner motor 203 and 204 simultaneously to form a 2-dimensional complex laser beam motion at the treating human skin target 208 as the Operator selects to use the Radiation Based device 24 shown in FIG. 1a. FIG. 3a is a schematic illustration of one preferred embodiment of a fractionated laser treatment pattern place on the desired treated tissue, in accordance with the present invention. The fractionated pattern comprises of a pre-determined plurality areas of the tissue that will be treated by the said laser pulsed energy and another plurality areas between the treated areas that remain healthy and untreated tissue to help the human body recovery process by leaving a bridge of healthy tissue between the treated areas. FIG. 3a illustrates the X and Y coordinates that are consistent with the coordinates on FIG. 2, 208. In the said preferred embodiment the Operator 25 (FIG. 1a) have selected from a pre-determined plurality of patterns and sizes, to use a ø15 mm hexagon pattern 300. The red aiming beam will show the outline of the selected hexagon treatment area boundary 300. When the operator 25 will press the foot switch 26 (FIG. 1a) the Radiation Based device will synchronized the movement of the scanner motors 203 and 204 (FIG. 2) to each location 301, placing laser pulses of particular pre-set properties at each location of the pre-determined plurality of locations within the outline boundary 300. In one preferred embodiment the pulse placement locations will start from the lowest right corner of the pattern 302, where the scanner motors 203 and 204 will hold position at 302 while the CPU Controller 22 will command the system to pulse one pre-set energy pulse selected by the operator 25. Once the pulse duration reached the end, the system CPU Controller 22 will command the scanner motors 203 and 204 to move the focused beam at the direction 305 consistent with move in X axis direction, from position 302 to position 303, the scanner motors 203 and 204 will hold position without any movement at location 303, and the CPU Controller 22 (FIG. 1a) will command the laser to pulse one pulse with a predetermined properties set by Operator 25 using the Touch Panel 10. At the end of the pulse duration at location 303, the system CPU Controller 22 will command the scanner motors 203 and 204 to move the focused beam again at the direction 305 consistent with move in X axis direction, from position 303 to position 304, the scanners motors will hold position without any movement at location 304, and the CPU Controller 22 (FIG. 1a) will command the laser to pulse one pulse with a predetermined properties set by Operator 25 using the Touch Panel 10. Once the laser pulse duration reached the end, the system will automatically advance to the next location along direction 305 as explained above to repeat the same process of stepping the scanner motors to move the focused laser beam to the new location, hold position in the new location while the CPU Controller 22 will command the laser to deliver one pre-programed pulse energy, repeating the process until position 306 pulse duration reached the end. At the end of the pulse at location 306, the system will command the scanner motors 203 and 204 to move the focused laser beam in the direction 307 which is moving one line up in the Y direction to position 308 where the scanner motors 203 and 204 will hold position while the system will deliver a single preset pulse. At the end of the pulse duration at position 308 the CPU Controller 22 will command the scanner motors 203 and 204 to move the focused laser beam along the negative x direction 310 from location 308 to location 309 repeating the same process of hold position while the laser deliver a pre-set energy pulse, and advance to the next adjacent position as explain above in great details. The entire plurality of pre-determined locations within the pattern boundaries will be delivered with the same pre-set laser pulse energy using the same step, hold position and repeat process. Once the plurality of pre-determined locations within the pattern boundaries have delivered the pre-set laser pulses, the CPU controller will resume presenting the red aiming beam outline 300 to indicate to the operator 25 that the placement of all pre-set pulses have been completed. The Operator 25 can then move the Handpiece 207 to the next area on the human tissue that needs to be treated to repeat the same process.

Figure 3B:
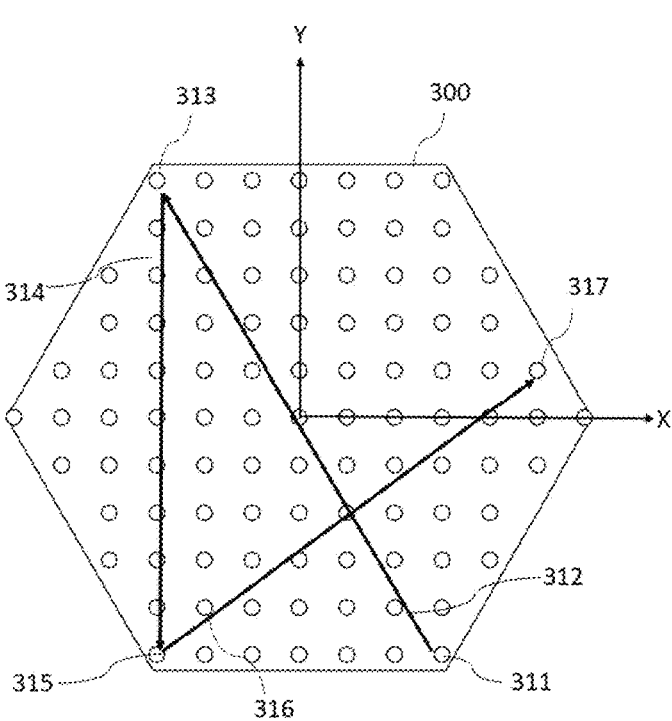

FIG. 3b is a schematic illustration of yet another preferred embodiment of a fractionated laser treatment pattern place on the desired treated tissue, in accordance with the present invention. In the said embodiment, the step, hold position and repeat process used to deliver the laser pulses to pre-program plurality of predetermined locations can be achieved by using random movement instead of cartesian movement along x and y axis as explain above. In the said preferred embodiment, the first pulse location will be 311, where the scanner motors 203 and 204 will hold position at 311 while the system will pulse one pre-set energy pulse selected by the operator 25. Once the pulse duration reached the end, the system CPU Controller 22 will command the scanner motors 203 and 204 to move the focused beam in synchronized movement along both x and y axis at the direction 312, from position 311 to position 313, the scanner motors 203 and 204 will hold position without any movement at location 313, while the system will pulse one pre-set energy pulse selected by the operator 25. Once the pulse duration reached the end, the system CPU Controller 22 will command the scanner motors 203 and 204 to move the focused beam in synchronized movement along the direction 314, from position 313 to position 315, the scanner motors 203 and 204 will hold position without any movement at location 315, while the system will pulse one pre-set energy pulse selected by the operator 25. Once the pulse duration reached the end, the system CPU Controller 22 will command the scanner motors 203 and 204 to move the focused beam in synchronized movement along the direction 316, from position 315 to position 317, the scanner motors 203 and 204 will hold position without any movement at location 317, while the system will pulse one pre-set energy pulse selected by the operator 25. Once the pulse duration reached the end the system CPU Controller 22 will continue the step, hold position, pulse the laser and repeat to place preset energy pulses in all pre-determined plurality of fractionate locations within the pattern boundaries as explain above.

The randomized movement algorithm to be used is of a kind of algorithm that will be keeping maximum physical distance between adjacent pulses to reduce any possibilities of accumulation of unwanted thermal injury, and for the other purpose reduce patient discomfort.

Figure 3C:
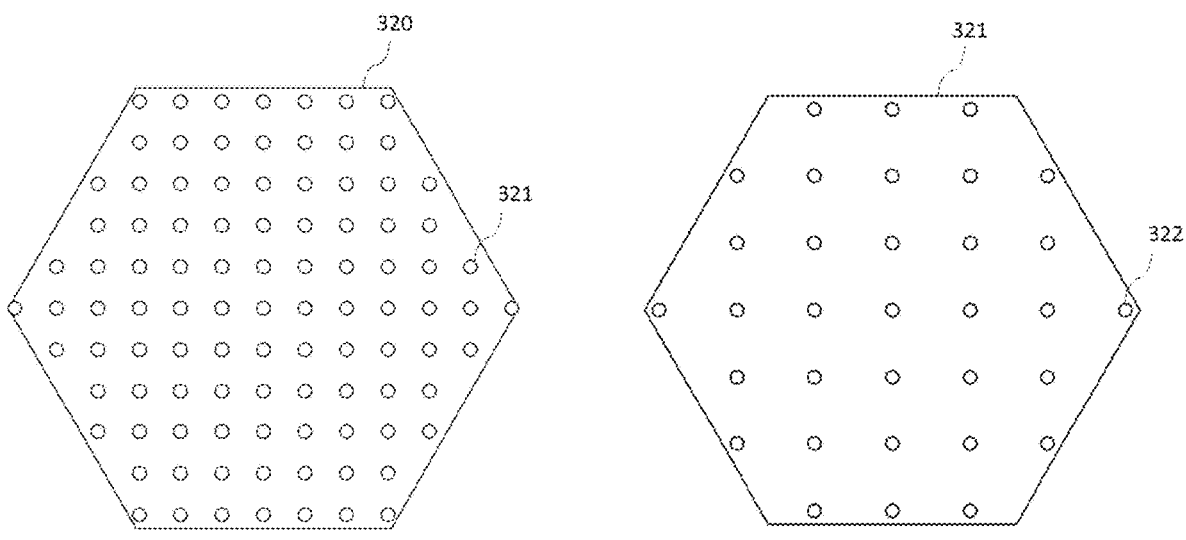

FIG. 3c illustrates the said preferred embodiment, where the Operator 25 can select from a pre-determined choices of available fractionated filling density of pulses from either pattern 320 or pattern 321, as an example. In the said preferred embodiment, pattern 320 and pattern 321 are of identical pattern type and size. The difference in said patterns 320 and 321 is that the density of pattern 320 is said to be of a higher density, there are larger number of pre-determined pulses locations in pattern 320 compared with pattern 321 that has smaller number of predetermined pulse locations, therefore, pattern 321 is said to be of a lower density.

Figure 3D:
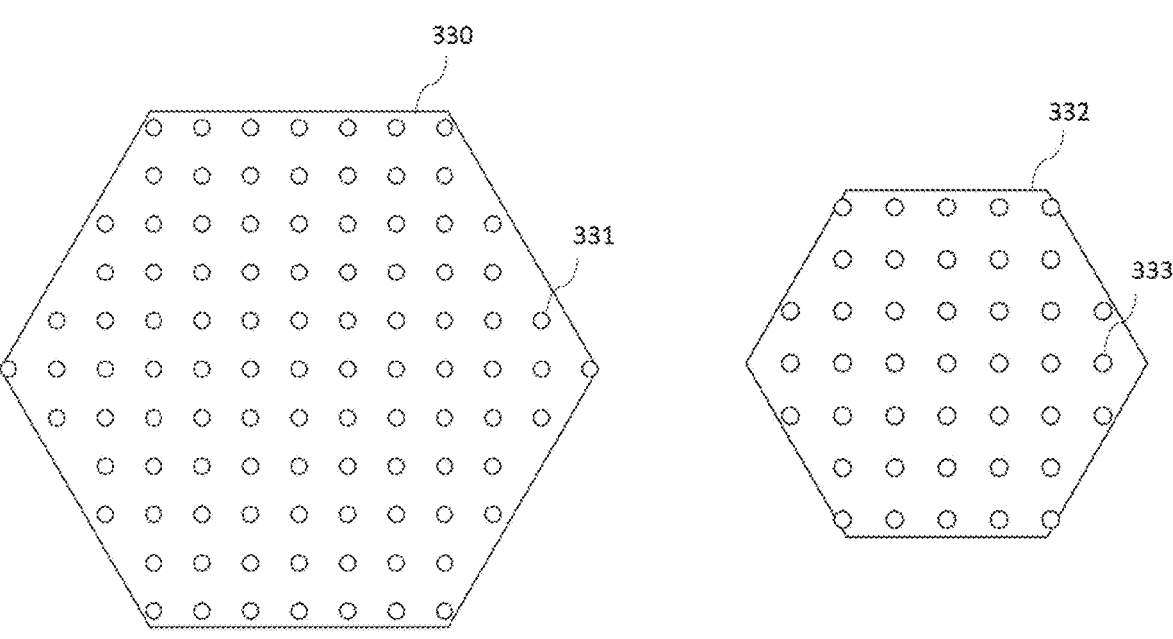

FIG. 3d illustrates the said preferred embodiment, the Operator 25 can select from a pre-determined choice of available plurality of fractionated pattern size with the same pulse density. The Operator 25 can select pattern size 330 or smaller size 332 comprising the same pulse density. The selection will be done by the Operator 25 using the Touch Panel 10 from a list of pre-programed available sizes and available pulse density.

In the said preferred embodiment the ability to easily change the pattern size and pulse density enables the Operator the flexibility to fit the particular laser pulse selection to the treated tissue type and tissue location in the body. As an example, when the Operator 25 will be using the said preferred embodiment Radiation Based device to treat facial skin around the human eyes, the choice of smaller patterns may increase the usefulness of the device in generating positive clinical results and reducing any risk of unwanted side effects, especially PIH.

Figure 4A:
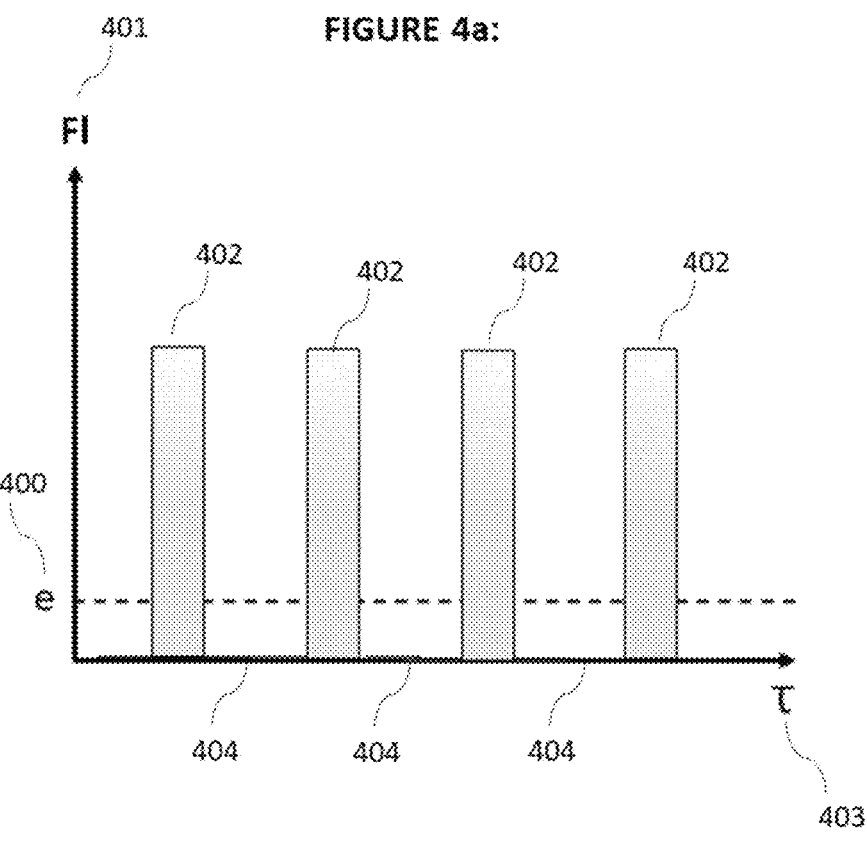
FIG. 4 a-c are graphs schematically illustrating a laser pulse sequence in accordance with the present invention.

FIG. 4a is a graph schematically illustrating a plurality of laser pulses sequence in accordance with the present invention. In the said graph the x denominator represents time scale as shown by 403, while the Y axis denominator illustrates fluence as shown by 401. The dash line illustrates the fluence threshold for human tissue ablation, denoted by 400. The fluence threshold, e, means that any pulse fluence that will be delivered to human tissue that is higher than "e", 400, will ablate the human tissue while any pulse with fluence below "e", 400, will not ablate the tissue but rather cause the energy to be absorbed by the human tissue and turn to heat in the said human tissue, which may cause thermal injury. The ablation threshold for human tissue is reported by many scientific papers, J. T Walsh "Er:YAG Laser Ablation of Tissue: Measurement of Ablation Rates" measured the ablation threshold fluence to be 2 joule/cm2. This publication established the fluence (energy density) relationship to ablation depth to follow this equation:

$$Fl = \frac{Z}{5.8} + 11$$

Fl—Laser Fluence, Joules/cm$^2$
Z—Laser ablation depth, μm (For ablation depth that is greater than 100 μm)
To define the energy per pulse there need to be use for the next equation:

$$E = \frac{Fl \times \pi Sz^2}{400,000}$$

E—Pulse energy, milli-Joules
Sz—Laser spot size, μm
In one preferred embodiment the laser is mid IR fiber laser operating at 2,940 nm with focused laser beam diameter of 120 μm. At the said preferred embodiment laser, the ablation threshold will be 0.23 milli-joule. Pulses 402 are preset to ablate human tissue to a selectable depth selected by Operator 25 programing the laser energy per pulse using the Touch Panel 10. Each of the plurality of pre-set laser pulses 402 will be delivered in each different location of the selected patter 300 (FIG. 3a) starting with pulse location 302 and to the next locations as explained herein above. The pulse duration of each pulse will be pre-set by the device CPU Controller 22 controlling the Laser device to deliver to the human tissue the exact amount of energy that is pre-programed by the Operator 25. The time duration between adjacent pulses 404, is another pre-set time duration that is controlled by the CPU Controller 22 to leave sufficient time for the Scanners motors 203 and 204 to move the mirror that reflects the said laser beam from location to the next location before the next pulse energy can be delivered to the next location. In the said preferred embodiment the plurality of pulse energy is pre-set by the Operator 25 based on the desired depth of ablation. In the said preferred embodiment, for ablation depth of 400 μm the Operator 25 will pre-set the plurality of laser pulse energy to be 9 milli-joules per individual pulse 402, based on the set calculations formulas above. In the said preferred embodiment the mid IR fiber laser maximum laser power is 10 watts, to generate pulse energy of 9 milli-joule per pulse the laser pulse duration will be set by CPU Controller 22 to be 0.9 milli-seconds, calculated by the following equation:

$$\tau = \frac{E}{P}$$

P—The laser power, watts
E—laser pulse energy, milli-joules
τ—Laser pulser duration, milli-seconds In yet another preferred embodiment when the pattern is placed on human facial skin for rejuvenation, the set energy per pulse may cause the patient discomfort due to the pulse duration especially if the Operator 25 will set the ablation depth to 1 mm or deeper.

Figure 4B:
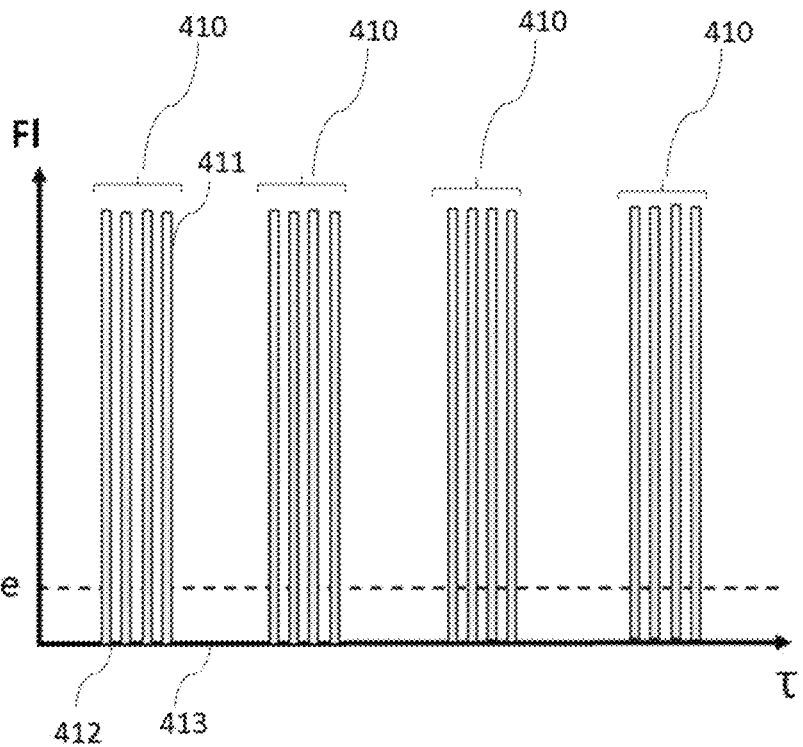

FIG. 4*b* is a graph schematically illustrating a plurality of a laser pulse sequence in accordance with the present invention. In yet another preferred embodiment, pulse 402 (FIG. 4*a*) that will be placed on patter 300 at a step and repeat process starting from location 302, will be divided to plurality of sub-pulses arranged in a pulse burst, 410, with pre-set time duration between each burst of sub-pulses 413 to be identical to the time duration delay 404 (FIG. 4*a*) as explained above when the System is using plurality of solid pulse 402 at each of the pre-determined plurality location withing the pattern boundaries. One advantage of plurality of sub-pulses arranged is pulse burst 410, is to lower patient discomfort as it will spread the energy per pulse over longer time duration and lower accumulation of unwanted thermal injury. In the said preferred embodiment example, the pulse burst 410 will include 4 sub-pulse 411 with pre-set time duration 412 between pulses 411, set by the CPU controller 22. In the said preferred embodiment in each location starting from 302 in the laser selected pattern 300 the system will deliver a burst of 4 sub pulses 410 with time delay 412 between each adjacent sub-pulses 411 for the same total energy per pulse burst 411, corresponding to the Operator 25 selection of the desired ablation depth, that can be calculated from the formulas disclosed above. The said preferred embodiment use a pulse burst with 4 sub-pulses as an example, the number of sub-is not limited to any particular number, pulse burst can include from 2 to "n" sub-pulses, depends on the clinical desired results. As noted in this application, in the said preferred embodiment the laser operates at 2,940 nm which is the peak water absorption, and the ablation of human tissue is very efficient since the human tissue contains over 70% of water. It is also noted by many clinical publications that at the said operating condition the ablation of human tissue will leave little to no thermal injury to the surrounding tissue thus the ablation zone is expected to follow with local bleeding as the laser ablated small blood vessels. This can be a desire effect in some clinical situations when the desired injury is of a pure mechanical nature, to replace as an example a use of micro-needles, especially if there may be a following use of drugs to efficiently deliver the medication to the tissue using the mechanical ablated injury.

Figure 4C:
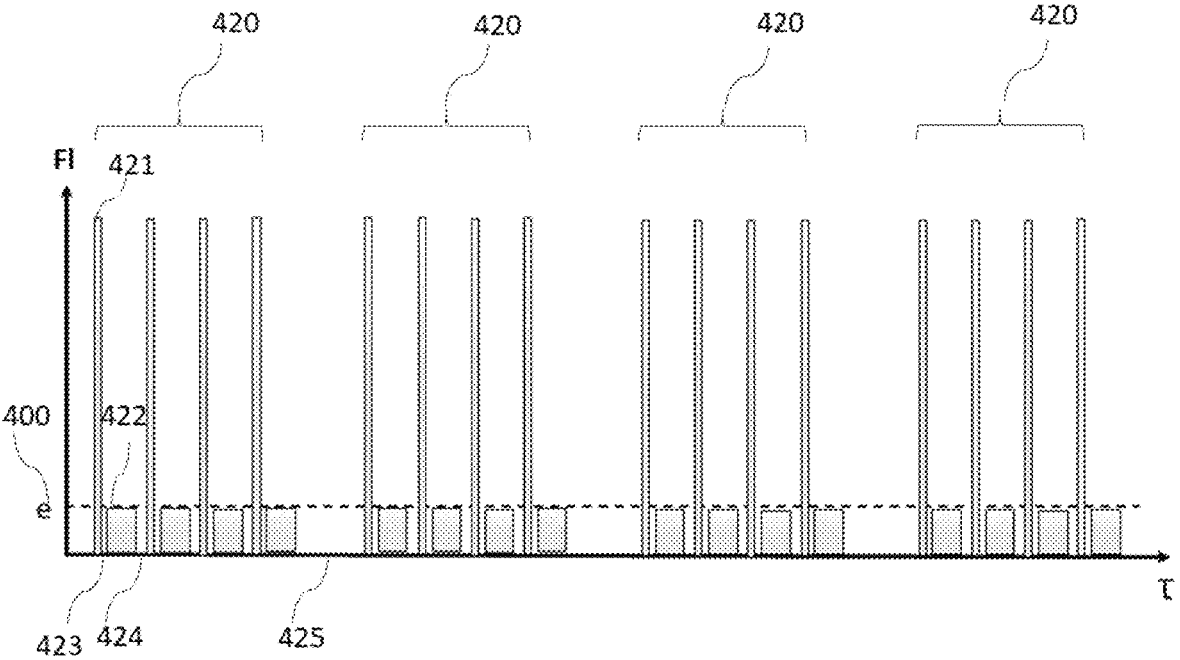

FIG. 4*c* is a graph schematically illustrating a plurality of a laser pulse sequence in accordance with the present invention. In this yet another preferred embodiment radiation based device pulse 402 (FIG. 4*a*) that will be placed on pattern 300 at a step and repeat process starting from 302, will be divided to a plurality of sub-pulses arranged as a pulse burst 420, different from the plurality of sub pulses burst 410 explained previously in this application. In the said preferred embodiment, the pulse burst 420 will be divided to 8 sub-pulse as an example, comprising of the first pulse 421, preset by CPU Controller 22 to be above ablation threshold "e" 400, following with the time delay 423 between pulse 421 and the next pulse, 422. Pulse 422 fluence is preset by the CPU controller 22 to be below the ablation threshold "e", 400, delivered by the radiation based device 18 operating at a lower laser power per pulse, as to generate fluence below the ablation Threshold "e", 400, thus not abating any human tissue but rather depositing the energy by heating up the surrounding tissue to create a coagulation effect and to form a controlled localized thermal injury. Following pulse 422 the CPU Controller 22 add another pre-program time delay 424 following the delivery of the next sub pulse 421 with the same preset fluence following with the time delay 423 and another pulse 422 with the same preset fluence below threshold "e", 400 . . . . In the said preferred embodiment the pulse burst 420 will include as an example, 4 ablating sub-pulses, 421 with preset fluence that is above ablation threshold "e", 400, and 4 coagulating sub pulses 422 with preset fluence that are under the ablation threshold "e", 400, with time delays 423 and 424 between pulses 421 and pulses 422 to complete the pulse burst for one location starting 302 at the patter 300. The next identical pulse burst 420 will be delivered to the next location in the pattern with pre-programed delay 425 that will be set by the CPU Controller 22 to allow sufficient time for the scanner motors 203 and 204 to complete the synchronized motion to direct the focus laser energy to the next location in the pattern 300. It is important to point out that the pulse burst 420, can be structured by the teaching of this invention to include any plurality of pulses in similar combination without limitation to the number of pulses in the burst. A pulse burst can include "n: number of ablative pulses and "N" number of coagulate pulses arranged in any other orders as the objective of this invention. The blending of ablating pulse energies with coagulating pulse energies in a pulse burst in accordance with the said preferred embodiment is in high desire in medical treatment of human tissue bringing important advantages; first advantage is when the apparatus is used to cut human tissue, blending coagulating pulses with the ablating-cutting pulses can prevent bleeding by coagulating the cut blood vessels, prevent contaminations and helps faster healing of the cut. Another advantage in blended pulses is when the apparatus is used on human skin particularly on the face, the apparatus can be used to deliver ablating pulses deep into the dermis, and deliver a blend of a pre-programed controlled amount of thermal injury that will reduce bleed and will generate maximize natural healing process following the treatment leading to effective skin rejuvenation without risks PIH or any other complications due to too much un-wanted thermal injury. Controlled fractionated thermal injuries in the dermis is the staple of facial rejuvenation, by stimulate formation of new collagen, new natural hyaluronic acid and in many patient it leads to creation of new elastin resulting in younger better looking skin.

Figure 5:
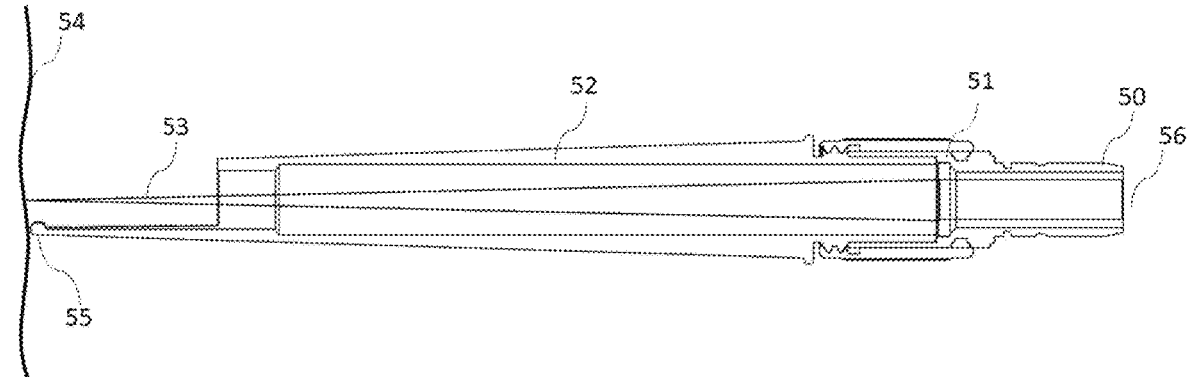
FIG. 5 is a schematic illustration of a surgical instrument for cutting and coagulating human tissue in accordance with the present invention.

FIG. 5 is a schematic illustration of a surgical instrument for cutting and coagulating human tissue in accordance with the present invention. In this yet another preferred embodiment the device is not using x-y scanner but instead a cutting and coagulation handpiece that will be moved over human tissue 54 by the Operator 25. The mounting shaft 50 connects the assembly to applicator mount quick disconnect 100 by replacing the said handpiece with Scanner Applicator 16 (FIG. 1a). The laser beam enters at the aperture 56 and propagate through focusing lens 51. The handpiece shaft 52 is used by the Operator 25 to hold the device, placing the tip pointer 55 in contact with the patient tissue 54 to direct the focused laser energy 53 to the human tissue to be treated. In the said preferred embodiment the Operator 25 may choose any of the 3 different pre-programed pulse type to cut and ablate human tissue while moving the handpiece manually. The advantages of the said preferred embodiment is that it can cut human tissue very efficiently without any thermal damage for treating sensitive human organs that can be easily damaged by any unwanted thermal injury. Such organs include human brain tissue, human vocal cords, human ocular tissue and others. In treating other less sensitive human tissue the Operator 25 can program the device to include a blend of coagulation and ablating pulses to achieve the clinical desired results as explained in this application.

Figure 6:
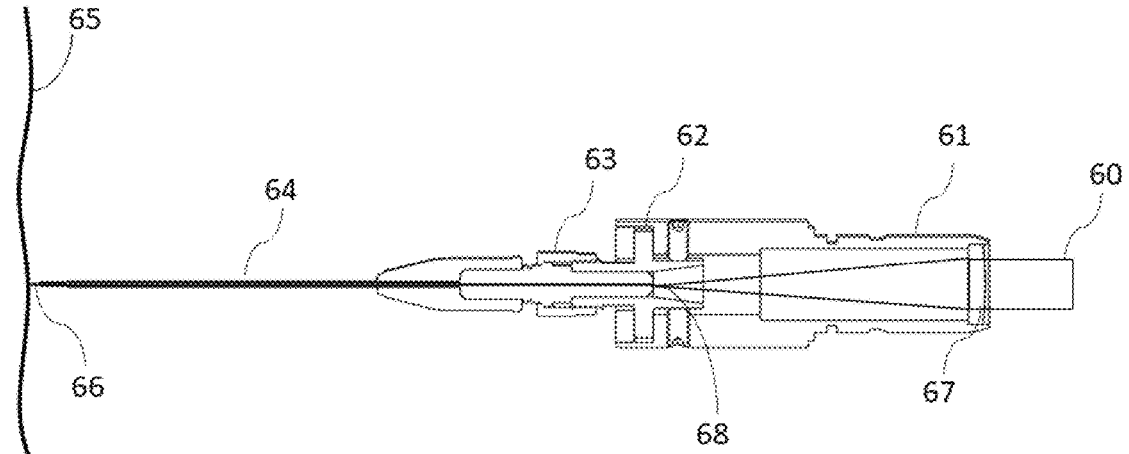
FIG. 6 is a schematic illustration of another surgical instrument using fiber optics for cutting a coagulating human tissue in accordance with the present invention.

FIG. 6 is a schematic illustration of yet another preferred embodiment comprising of another surgical instrument using fiber optics for cutting and coagulating human tissue in accordance with the present invention. In this preferred embodiment the use of fiber optics enables to deliver the laser energy to human tissue in cavities or human body parts that have limited physical access, such as human ear, nose, throat or ocular tissue. The said fiber optic device will be mounted using shaft 61 to connect with quick disconnect 100. The laser beam 60 will propagate through another focusing optics 67 with the laser energy focused on the face of the fiber optics 78. The fiber optics connector 63 is mounted on the housing 62 that can be aligned the fiber optics center line to be concentric with the laser focus beam 68. The said fiber optics is mounted inside a stainless-steel metal tube 64 to protect the fiber optics from breaking during the use by Operator 25 inside human cavity treating human tissue. In the preferred embodiment the fiber optics is made of a Sapphire with core diameter of 140 μm with similar spot size to treat human tissue as the focused scanner beam. In the said preferred embodiment the advantage is the ability to access and deliver the laser energy to human tissue in tight locations. Using the blended pulses can also increase the effectiveness of ablative tissue treatment in areas with tight access without depositing unwanted thermal damage, and in a different preset of blended pulses the apparatus can deliver a pre-programmed amount of coagulation and thermal damage to achieve the desired clinical results even in places with very challenging physical access.

What we claim is:

1. A laser surgical apparatus for performing treatment by irradiating a part to be treated by a variable pulsed laser beam comprising:

a. a laser source configured to emit optical energy at a laser wavelength in a range of 2,700 nm to 3,500 nm; and b. a fractional optical treatment system configured to deliver an optical focused beam emitted by the laser source to a plurality of predetermined locations in a target area of human skin, the fractional optical treatment system including at least a controller, an energy calibration device, and an applicator, wherein the controller is configured to control the laser source and the applicator to perform the treatment according to user input, the controller being configured to enable a user to select at least one of:

i. a size of the optical focused beam at a surface of the human skin, ii. a shape of the optical focused beam at the surface of the human skin, iii. a pattern density of the predetermined locations in the target area, or iv. an algorithm for moving the optical focused beam between the plurality of predetermined locations, and wherein the controller is further configured to enable the user to pre-program a pulse burst having a plurality of temporally spaced-apart sub-pulses, the pulse burst being delivered to each of the plurality of predetermined locations in the target area, the spaced-apart sub-pulses of the pulse burst comprising a plurality of ablative sub-pulses and a plurality of non-ablative sub-pulses, each of the ablative sub-pulses being temporally spaced apart from another of the ablative sub-pulses by one or more of the non-ablative sub-pulses, each of the ablative sub-pulses being identical to the other ablative sub-pulses and having a fluence between 2 to 100 Joules/cm$^2$ and configured to ablate the human skin, each of the non-ablative sub-pulses being identical to the other non-ablative sub-pulses and having a fluence between 0.1 to 2.0 Joules/cm$^2$ and configured to form a controlled localized thermal injury by depositing energy through heating the human skin without ablating the human skin, and wherein the energy calibration device is configured to sample the beam emitted by the laser source and communicate with the controller in a closed loop to control energy delivered by the laser source to match energy set by the user.

2. The apparatus of claim 1, wherein the controller is configured to enable the user to select the size of the optical focused beam at a surface of the human skin.

3. The apparatus of claim 1, wherein the controller is configured to enable the user to select the shape of the optical focused beam at the surface of the human skin.

4. The apparatus of claim 1, wherein the controller is configured to enable the user to select the pattern density of the predetermined locations in the target area.

5. The apparatus of claim 1, wherein the controller is configured to enable the user to select the algorithm for moving the optical focused beam between the plurality of predetermined locations, wherein the user is enabled to select from Cartesian order movement, wherein the optical focused beam is moved sequentially between adjacent ones of the predetermined locations, and randomized order movement wherein the optical focused beam is moved between the predetermined locations in a random order.

6. The apparatus of claim 1, wherein the sub-pulses in the pulse burst are separated from each other by a time duration between 50 to 5,000 micro-seconds.

7. The apparatus of claim 1, wherein the laser source is a mid infrared fiber laser and the laser wavelength is in a range of 2,800 nm to 2,950 nm.

8. A laser surgical apparatus for performing treatment by irradiating a part to be treated by a variable pulsed laser beam comprising:

a. a laser source configured to emit optical energy at a laser wavelength in a range of 2,700 nm to 3,500 nm;

b. a fiber optic configured to deliver an optical focused beam emitted by the laser source to a target area of human skin;

c. a controller configured to control the laser source to perform the treatment via the fiber optic according to user input, the controller being configured to enable a user to pre-program a pulse burst having a plurality of temporally spaced-apart sub-pulses, the spaced-apart sub-pulses of the pulse burst comprising a plurality of ablative sub-pulses and a plurality of non-ablative sub-pulses, each of the ablative sub-pulses being temporally spaced apart from another of the ablative sub-pulses by one or more of the non-ablative sub-pulses, each of the ablative sub-pulses being identical to the other ablative sub-pulses and having a fluence between 2 to 100 Joules/cm$^2$ and configured to ablate the human skin, each of the non-ablative sub-pulses being identical to the other non-ablative sub-pulses and having a fluence between 0.1 to 2.0 Joules/cm$^2$ and configured to form a controlled localized thermal injury by depositing energy through heating the human skin without ablating the human skin; and d. an energy calibration device configured to sample the beam emitted by the laser source and communicate with the controller in a closed loop to control energy delivered by the laser source to match energy set by the user.

9. The apparatus of claim 8, wherein the sub-pulses in the pulse burst are separated from each other by a time duration between 50 to 5,000 micro-seconds.

10. The apparatus of claim 8, wherein the laser source is a mid infrared fiber laser and the laser wavelength is in a range of 2,800 nm to 2,950 nm.

11. The apparatus of claim 8, wherein the fiber optic is made of Sapphire.

12. The apparatus of claim 11, wherein the Sapphire fiber optic has a diameter in the range of 100 μm to 250 μm.

\* \* \* \* \*